United States Patent [19]

Lister

[11] Patent Number: 5,087,450

[45] Date of Patent: Feb. 11, 1992

[54] VIRUCIDAL WIPE CONTAINING HYPOCHLORITE WITH HAND PROTECTIVE BARRIER

[76] Inventor: Mark W. Lister, 709 NE. 20th St., Wilton Manors, Fla. 33305

[21] Appl. No.: 504,616

[22] Filed: Apr. 4, 1990

[51] Int. Cl.$^5$ .................. A61K 33/14; A61L 2/16; B32B 17/04; B65D 30/26
[52] U.S. Cl. .................. 424/402; 424/404; 424/405; 424/409; 424/661; 424/665; 424/443; 424/446; 428/286; 428/288; 428/289; 206/361
[58] Field of Search .............. 424/402, 404, 443, 661; 604/375; 428/288

[56] References Cited

U.S. PATENT DOCUMENTS

| | | | |
|---|---|---|---|
| 3,057,467 | 10/1962 | Williams | 206/361 |
| 4,767,788 | 8/1988 | Diana | 424/443 |
| 4,773,904 | 9/1988 | Nakanishi et al. | 604/375 |
| 4,917,238 | 4/1990 | Schumacher | 206/223 |

Primary Examiner—Thurman K. Page
Assistant Examiner—Edward J. Webman
Attorney, Agent, or Firm—Malin, Haley, McHale, DiMaggio & Crosby

[57] ABSTRACT

A virucidal wipe for manually removing human organic material contaminated with HIV (AIDS), herpes or hepatitis viruses from and disinfecting surfaces such as countertops, floors, walls, instruments and plastic bed liners. The virucidal wipe includes a gauze pad impregnated with a 10% sodium hypochlorite solution and a hand-held flexible non-porous plastic barrier firmly attached thereto to protect the user from viral contamination and the sodium hypochlorite. The product includes a protective package to store the wipe prior to use.

2 Claims, 1 Drawing Sheet

VIRUCIDAL WIPE CONTAINING HYPOCHLORITE WITH HAND PROTECTIVE BARRIER

BACKGROUND OF THE INVENTION

1. Field of the Invention

A virucidal wipe for disinfecting surface areas from viral contaminants including Human Immunodeficiency Virus (HIV) (AIDS), herpes, and hepatitis that has a disinfectant/fluid impervious barrier to protect the hands of the user.

2. Discussion of the Prior Art

The advent of the HIV (AIDS) virus has made exposure to human blood and other body fluids potentially fatal to doctors, hospital and clinic technicians, health care workers, and other hospital patients. Herpes and hepatitis B virus also can pose major disease problems to those exposed from direct or indirect blood contamination or other body fluids. Of specific concern is the effective removal of blood spills from various surfaces found in a hospital or laboratory environment. The problem has been to determine an effective means of removing viral contaminated blood, plasma, serum or other body fluids without further endangering the person cleaning the surfaces. In U.S. Pat. No. 4,578,119 issued to Marcus et al. on Mar. 25, 1986, a solid composition is shown for absorbing liquid and destroying pathogen activity. This composition is dumped over the blood spill and then removed as a solid material. A single wipe that does not require the removal of additional solid materials would be much more practical and desirable. A virucidal wipe is shown in U.S. Pat. No. 4,355,021 issue to Mahl et al. on Oct. 19, 1982 that is employed as a nasal wipe to reduce transmission of viral diseases by the hands. Another virucidal nasal wipe is disclosed in U.S. Pat. No. 4,828,912 issued to Hossain et al. which includes the use of impregnated substrates of facial tissues or non-woven materials. Clearly these wipes are not suitable for cleaning or removing viral contaminated blood or body fluids from surfaces because of the potential danger of exposure to the user.

The present invention overcomes the problems of the prior art by providing a virucidal wipe that includes a porous pad of gauze impregnated with an effective virucide (sodium hypochlorite) affixed to a liquid impervious, non-porous backing (barrier).

SUMMARY OF THE INVENTION

A virucidal wipe for disinfecting viral contaminants such as HIV (AIDS), herpes, and hepatitis B, while removing blood or other body fluids from surfaces. The wipe includes a porous substrate impregnated with a 10% sodium hypochlorite solution and a hand protective liquid impervious flexible backing connected to the porous substrate to prevent or reduce exposure of the skin from either contaminant or disinfectant.

The porous substrate selected could be a gauze pad impregnated with the 10% sodium hypochlorite solution.

The liquid impervious backing could be constructed of a plastic sheet that is fused or glued to one side of the gauze pad.

The sodium hypochlorite solution has been found effective in disinfecting and destroying the HIV (AIDS) virus along with herpes and hepatitis. The percentage of solution can be varied depending on the particular environment of intended use hospital, clinic, laboratory, or home, and the anticipated viral contaminants.

The wipe is suitable for use at any public or private facility or environment that expects blood or body fluid contamination or spills on surface areas that are used or accessed by people. These could include hospitals, doctors' offices, clinics, technical medical laboratories, public facilities including rest rooms, and private home usage.

The size and thickness of each viral wipe can vary, dependent upon the surface and area to be cleaned and the amount of contaminant (organic matter) to be removed from the surface area. The backing could include a hand attachment or glove attachment.

Because the 10% sodium hypochlorite solution becomes unstable within a short period of time, the invention includes a storage package to store each wipe until the wipe is ready for use. Essentially each side of the storage package includes an inner liner of plastic, a middle layer of foil and an outer layer of paper.

It is an object of this invention to provide an effective viral wipe for ridding surfaces of viral contaminants such as HIV (AIDS), herpes, and hepatitis found in human body fluids such as blood.

It is another object of this invention to provide a viral wipe that can be safely used for manually cleaning a surface containing virally contaminated human body fluids.

And yet another object of this invention is to provide a low cost viral wipe, non-complex in construction that can be used to safely and effectively clean surfaces contaminated with body fluids that include HIV (AIDS), herpes or hepatitis viruses.

In accordance with these and other objects which will be apparent hereinafter, the instant invention will now be described with particular reference to the accompanying drawings.

PREFERRED EMBODIMENT OF THE INVENTION

Figure 1:
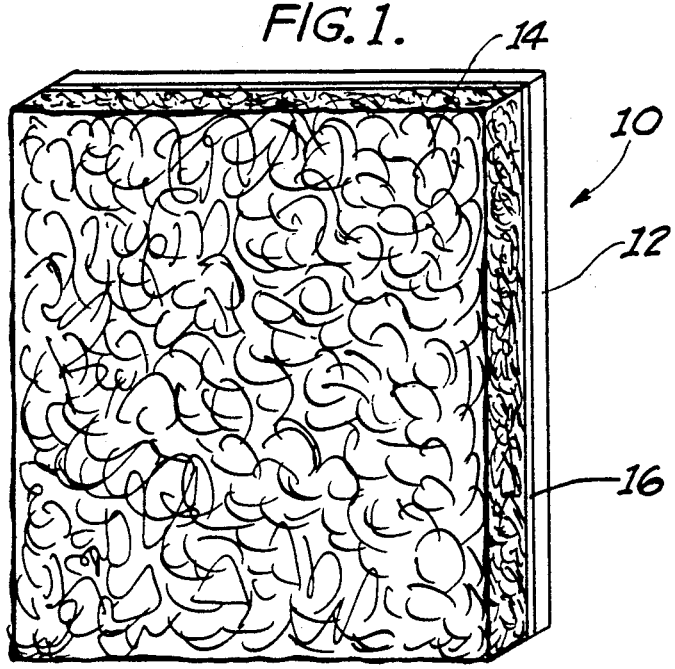
FIG. 1 shows a perspective view of the viral wipe in accordance with the invention.

Referring now to the drawings and specifically FIG. 1, the invention without the protective package is shown as a viral wipe 10 comprising a flexible, fluid impervious plastic barrier 12 firmly fixed to a gauze pad 14 that has been impregnated with a 10% sodium hypochlorite solution. The gauze pad 14 could be attached to the flexible barrier 12 by fusion or a suitable adhesive. The thickness of the gauze pad 14 can be varied as can be the length and width of the wipe dependent upon the nature of the surface to be cleaned and the kind and amount of organic material to be removed (i.e., blood, mucous, or other body fluid).

Figure 2:
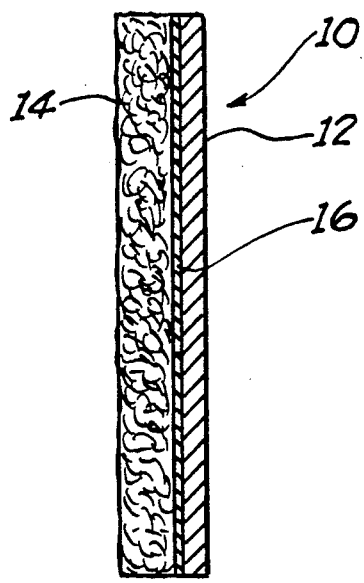
FIG. 2 shows a cross-sectional view in elevation of the viral wipe shown in FIG. 1.

FIG. 2 shows the viral wipe 10 and the fusion or adhesive layer 16 that attaches the flexible plastic barrier 12 to the gauze pad 14.

Figure 3:
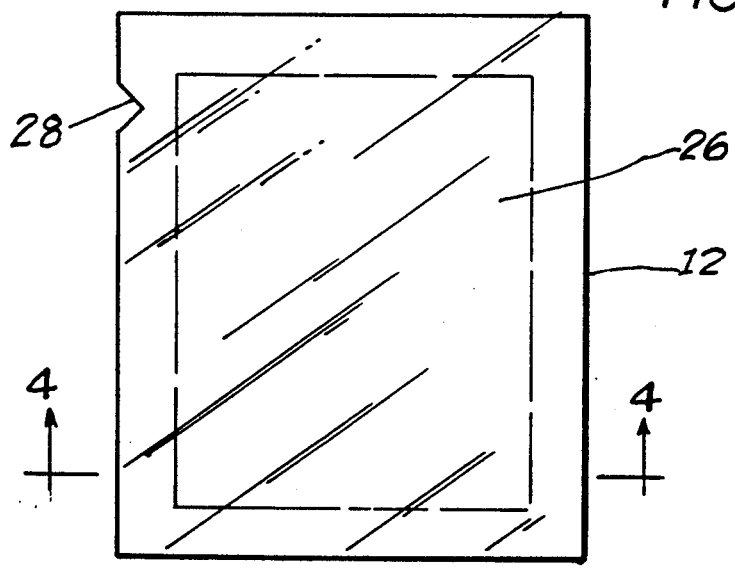
FIG. 3 shows a front cross-sectional view of the protective package used to store the viral wipe shown in FIG. 1.
Figure 4:
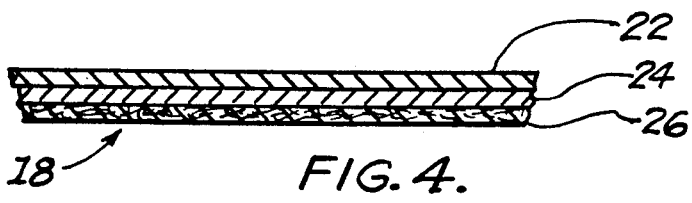
FIG. 4 shows a cross-sectional view of the side wall of the protective package shown in FIG. 3.

FIG. 3 shows the one side panel 18 of a protective package for storing the viral wipe of FIG. 1. The panel 18 includes an inner plastic lining sheet 26 with a border 20 that represents either fusion method or a suitable glue used to attach the panel 18 to an identical panel to form a two-sided closed and sealed package. The panel 18 is shown in FIG. 4 comprised of an outer paper lining 22, a foil lining 24 and a plastic lining 26 which forms the inside lining of the closed package. The package prevents the loss or evaporation of the sodium hypochlorite that is impregnated in the gauze pad 14. Once packaged, the viral wipe 10 constitutes a self-contained effective viral disinfectant that needs no additional virucidal compositions and can be safely stored, ready for use in a hospital, laboratory, public facility, or private home.

To use the viral wipe 10, the notch 28 permits access to separate the package panels 18 in order to remove the viral wipe 10 from the sealed package. Once removed, the viral wipe is grasped on the flexible barrier 12 which shields the operator's hand from both the contaminated organic material to be removed and the sodium hypochlorite. The barrier 12 can also protect the user from micro particles such as glass.

Although the invention has been disclosed using a 10% hypochlorite solution as the virucide, the concentration could be varied to accommodate a specific environment or virus. Concentrates could be varied from 1% to greater than 50% if required.

The viral wipe may be used to remove organic materials from counter tops, walls, floors, instruments not corroded by sodium hypochlorite, plastic bed linings, restroom fixtures and numerous other surfaces. The viral wipe can be used in any facility that could anticipate the clean up and removal of contaminated body fluids having HIV (AIDS), herpes or hepatitis viruses.

Although the gauze pad 14 has been shown, the viral wipe could utilize any porous, sturdy material that can receive the sodium hypochlorite solution and act as a surface applicator and cleaner.

The instant invention has been shown and described herein in what it is considered to be the most practical and preferred embodiment. It is recognized, however, that departures may be made therefrom within the scope of the invention and that obvious modifications will occur to a person skilled in the art.

What I claim is:

1. A viral wipe to remove organic material having viral containments from a surface comprising:

a gauze porous layer forming a pad;

a plastic non-porous flexible fluid impervious layer firmly affixed and fused on one side to said porous layer;

said porous layer impregnated with an aqueous solution of sodium hypochlorite in an amount to be effective as a virucide against HIV (AIDS), herpes or hepatitus viruses;

a protective package for storing said viral wipe that prevents escape of said sodium hypochlorite;

said protective package comprising of first and second panels, each panel including an inner plastic sheet, an intermediate foil sheet and an outer paper sheet, said panels being joined together around their perimeters to form a sealed chamber for receiving said viral wipe, said protection package including a notch means for ease of removal of said viral wipe.

2. A viral wipe as in claim 1, wherein:

said porous pad is impregnated with an aqueous solution of about 10% sodium hypochlorite.

* * * * *